US010139376B2

(12) United States Patent
Hershey et al.

(10) Patent No.: US 10,139,376 B2
(45) Date of Patent: Nov. 27, 2018

(54) SYSTEM FOR SENSING AND LOCATING DELAMINATION

(71) Applicant: General Electric Company, Schenectady, NY (US)

(72) Inventors: John Erik Hershey, Ballston Lake, NY (US); Frederick Wilson Wheeler, Niskayuna, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 300 days.

(21) Appl. No.: 15/087,416

(22) Filed: Mar. 31, 2016

(65) Prior Publication Data

US 2017/0284974 A1    Oct. 5, 2017

(51) Int. Cl.
*G01N 29/44* (2006.01)
*G08B 21/18* (2006.01)
(Continued)

(52) U.S. Cl.
CPC ........... *G01N 29/449* (2013.01); *G01N 29/04* (2013.01); *G01P 15/001* (2013.01);
(Continued)

(58) Field of Classification Search
CPC .............................. G01N 29/449; G01N 29/04
(Continued)

(56) References Cited

U.S. PATENT DOCUMENTS 5,814,729 A    9/1998 Wu et al.
8,144,005 B2   3/2012 Hu et al.
(Continued)

FOREIGN PATENT DOCUMENTS

CN    101000294 A    7/2007
CN    102680578 A    9/2012
DE    102005052644 A1 5/2007

OTHER PUBLICATIONS

Marantidis, C. et al., "Acoustic-emission sensing in an on-board smart structural health monitoring system for military aircraft", Proc. SPIE 2191, Smart Structures and Materials 1994: Smart Sensing, Processing, and Instrumentation, vol. 2191, May 1, 1994, (pp. 258-264, 7 total pages).

(Continued)

*Primary Examiner* — Anthony Ho
(74) *Attorney, Agent, or Firm* — GE Global Patent Operation; Nitin Joshi (57) ABSTRACT

A system to monitor a composite system component may include a plurality of sensors mounted proximate to the composite system component. A signal processing unit may receive, from each of the plurality of sensors, a series of sensed values associated with the composite system component and determine a kurtosis value for each series of sensed values. A threshold exceedance detector may detect if at least one of the kurtosis values exceeds a pre-determined threshold value. A delamination location estimation unit may calculate an estimated location of a composite system component delamination alert signal based on calculated time difference delay values of detected signal impulses in the series of sensed values using at least four of the plurality of sensors. A delamination alert output may then transmit a composite system component delamination alert signal, along with the estimated location, when at least one of the kurtosis values exceeds the pre-determined threshold.

16 Claims, 10 Drawing Sheets

(51) Int. Cl.
  *G01N 29/04* (2006.01)
  *G01P 15/00* (2006.01)
(52) U.S. Cl.
  CPC ..... *G08B 21/182* (2013.01); *G01N 2291/023* (2013.01); *G01N 2291/0289* (2013.01)
(58) Field of Classification Search
  USPC ........................................................ 702/182
  See application file for complete search history.

(56) References Cited

U.S. PATENT DOCUMENTS

| | | | |
|---|---|---|---|
| 8,176,786 | B2 | 5/2012 | Sohn et al. |
| 8,707,787 | B1 | 4/2014 | Sohn et al. |
| 8,914,244 | B2 | 12/2014 | Kollgaard et al. |
| 2009/0300417 | A1* | 12/2009 | Bonissone ......... G05B 23/0254 714/26 |
| 2015/0185128 | A1 | 7/2015 | Chang et al. |

OTHER PUBLICATIONS

Yarlagadda, R. et al., "GPS GDOP metric", Radar, Sonar and Navigation, IEE Proceedings—Radar, vol. 147, Issue: 5, Oct. 2000, (pp. 259-264, 6 total pages).

Dubois, Thierry, "Jet blast damaged controls of Air Moorea Twin Otter", http://www.ainonline.com/aviation-news/aviation-international-news/2008-12-30/jet-blast-damaged-controls-air-moorea-twin-otter, Dec. 30, 2008, 2pgs.

Moslehi B et al., "Multifunctional Fiber Bragg Grating sensing system for load monitoring of composite wings", Aerospace Conference, 2011 IEEE, Mar. 5-12, 2011, Big Sky, MT, (pp. 1-9, 9 total pages).

Li, Dongsheng et al., "Fatigue Damage Evolution and Monitoring of Carbon Fiber Reinforced Polymer Bridge Cable by Acoustic Emission Technique", International Journal of Distributed Sensor Networks, vol. 2012, Article ID: 282139, Aug. 13, 2012, DOI: 10.1155/2012/282139, 8pgs.

* cited by examiner

SYSTEM FOR SENSING AND LOCATING DELAMINATION

BACKGROUND

It is often desirable to make assessment and/or predictions regarding the operation of a real world physical system, such as an electro-mechanical system. For example, it may be helpful to predict a Remaining Useful Life ("RUL") of an electro-mechanical system, such as an aircraft body part, to help plan when the system should be inspected or repaired. Likewise, an owner or operator of a system might want to monitor a condition of the system, or a portion of the system, to help make maintenance decisions, budget predictions, etc. Even with improvements in sensor and computer technologies, however, accurately making such assessments and/or predictions can be a difficult task. For example, an event that occurs while a system is not operating might impact the RUL and/or condition of the system but not be taken into account by typical approaches to system assessment and/or prediction processes.

By way of example, consider a composite laminate structure, which might comprise layers of fibrous composite materials which can be joined to provide appropriate structural properties, such as in-plane stiffness, bending stiffness, strength, coefficient of thermal expansion, etc. The individual layers may comprise high-modulus, high-strength fibers (e.g., graphite, glass, boron, or silicon carbide) using polymeric, metallic, and/or ceramic matrix materials (e.g., epoxies, polyimides, aluminum, titanium, and alumina). Composite laminate structures are increasingly used in aircraft construction, and inadvertent damage to such structures, such as "delamination," may represent an air safety concern (e.g., when the laminate structure is associated with a tail section of an airplane). As used herein, the term "delamination" may refer to a mode of failure for composite materials. In laminated materials, repeated cyclic stresses, impacts, etc. may cause layers to separate, which can form a mica-like structure of separate layers, with significant loss of mechanical toughness. Such delamination damage may impact the RUL of a system, require further investigation, etc. Note that delamination might not be noticeable by visual inspection, and detecting delamination damage can be a difficult process.

Moreover, in order to compute the RUL of a system, it may be necessary to know or assess a highly multi-dimensional state of a system. Note that the state of the system could change dramatically even when the system is not in operation (or is not operating in its most stressful mode). For example, an aircraft that is parked or taking on fuel, baggage, or passengers would not be expected to encounter as harsh an environment as it would during flight. There may be, however, cases where significant changes to an aircraft's health can occur during non-flight periods. For example, in at least one aircraft a pitch-up control cable was damaged while the controls were locked (and the plane was parked) because another aircraft taxied nearby resulting in exhaust that blasted the parked plane. This caused a force between 0.2 and 2.8 times the limit load on the pitch-up cable and even a single exposure was thought to be enough to break the cable. Another example may be associated with low speed collisions of a parked aircraft with a ground service equipment vehicle (such as a baggage delivery vehicle or a fuel truck). Ground service equipment interactions are responsible for most of the damage to commercial transport aircraft and it is estimated that half of the damage is due to collisions with baggage vehicles. These collisions may be associated with blunt impacts and may affect a significant area (and involve multiple elements hidden within the structure). Such collisions might leave no more than minimal visual signs of damage yet may still be deleterious to both aluminum and carbon-epoxy composite materials.

It would therefore be desirable to provide systems and methods to facilitate delamination assessments and/or predictions for a physical system in an automatic and accurate manner.

SUMMARY

According to some embodiments, a system to monitor a composite system component may include a plurality of sensors mounted proximate to the composite system component. As a non-limiting illustration and example, the sensors herein may comprise acoustic transducers.

A signal processing unit may receive, from each of the plurality of sensors, a series of sensed values associated with the composite system component and determine a kurtosis value for each series of sensed values. A threshold exceedance detector may detect if at least one of the kurtosis values exceeds a pre-determined threshold value. A delamination location estimation unit may calculate an estimated location of a composite system component delamination alert signal based on calculated time difference delay values of detected signal impulses in the series of sensed values using at least four of the plurality of sensors. A delamination alert output may then transmit a composite system component delamination alert signal, along with the estimated location, when at least one of the kurtosis values exceeds the pre-determined threshold.

Some embodiments comprise: means for receiving by a signal processing unit a series of sensed values, associated with the composite system component, from each of a plurality of sensors mounted proximate to the composite system component; means for determining by the signal processing unit a kurtosis value for each series of sensed values; means for detecting, by a threshold exceedance detector, if at least one of the kurtosis values exceeds a pre-determined threshold value; means for calculating, by a delamination location estimation unit, an estimated location of a composite system component delamination alert signal based on calculated time difference delay values of detected signal impulses in the series of sensed values using at least four of the plurality of sensors; and means for transmitting, via a delamination alert output, a composite system component delamination alert signal, along with the estimated location, when the at least one of the kurtosis values exceeds the pre-determined threshold.

Some technical advantages of some embodiments disclosed herein are improved systems and methods to facilitate delamination assessments and/or predictions for a physical system in an automatic and accurate manner.

DETAILED DESCRIPTION

In the following detailed description, numerous specific details are set forth in order to provide a thorough understanding of embodiments. However it will be understood by those of ordinary skill in the art that the embodiments may be practiced without these specific details. In other instances, well-known methods, procedures, components and circuits have not been described in detail so as not to obscure the embodiments.

Figure 1:
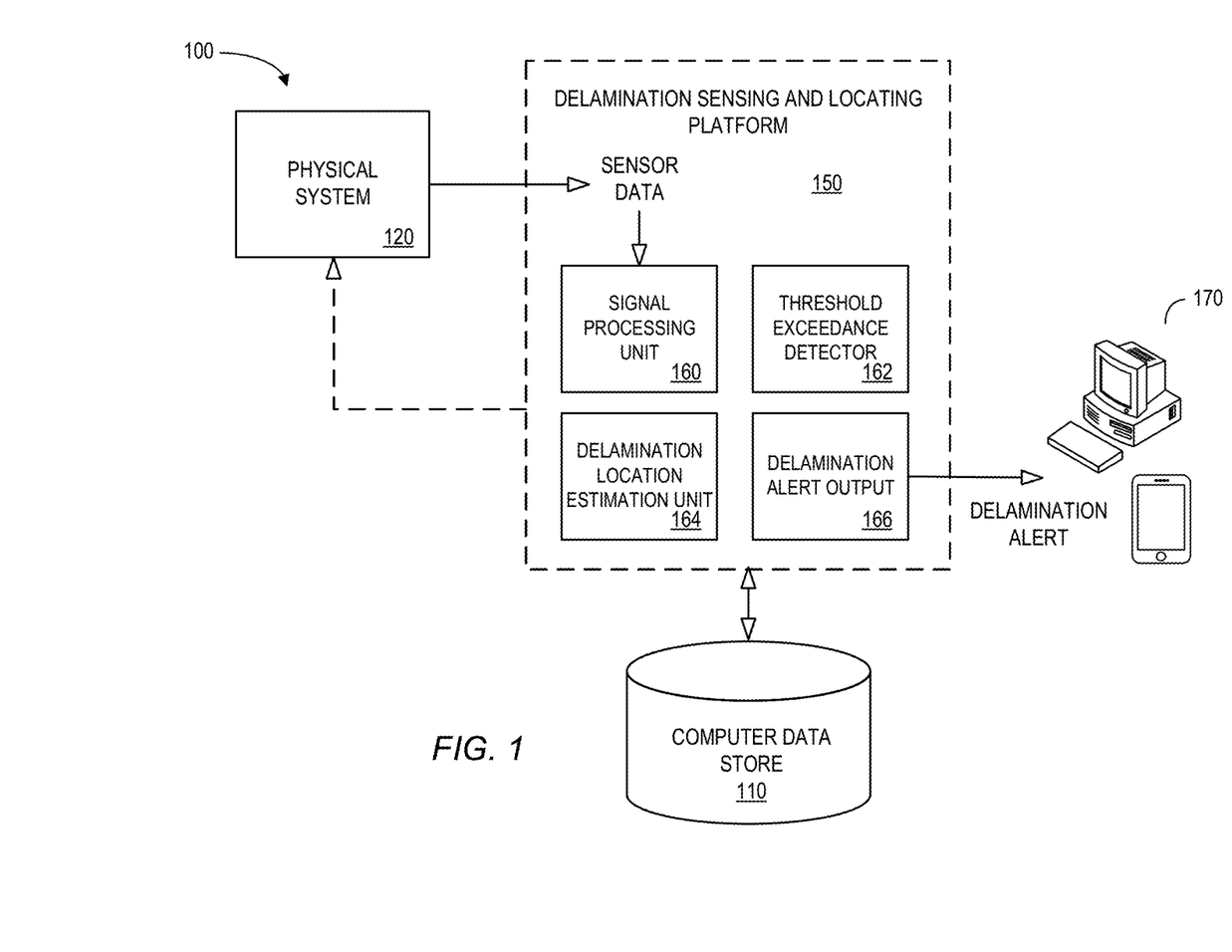
FIG. 1 is a high-level block diagram of a system that may be provided in accordance with some embodiments.

It is often desirable to make assessment and/or predictions regarding the operation of a real world physical system, such as an electro-mechanical system. For example, it may be helpful to predict the Remaining Useful Life ("RUL") of an electro-mechanical system, such as an aircraft body part, to help plan when the system should be replaced. In some cases, an expected useful life of a system may be estimated by a calculation process involving the probabilities of failure of the system's individual components, the individual components having their own reliability measures and distributions. FIG. 1 is a high-level architecture of a system 100 in accordance with some embodiments. The system 100 may include a computer data store 110 that provides information to a delamination sensing and locating platform 150. Data in the data store 110 might include, for example, information about a physical system 120, such as historic aircraft body part and sensor information and/or prior delamination events.

The delamination sensing and locating platform 150 may, according to some embodiments, access the data store 110 and/or receive sensor data from the physical system 120 to create a delamination alert that may be transmitted to various user platforms 170 as appropriate (e.g., for display to a user). As used herein, the term "automatically" may refer to, for example, actions that can be performed with little or no human intervention. According to some embodiments, information about the delamination alert may be transmitted back to the physical system 120.

As used herein, devices, including those associated with the system 100 and any other device described herein, may exchange information via any communication network which may be one or more of a Local Area Network ("LAN"), a Metropolitan Area Network ("MAN"), a Wide Area Network ("WAN"), a proprietary network, a Public Switched Telephone Network ("PSTN"), a Wireless Application Protocol ("WAP") network, a Bluetooth network, a wireless LAN network, and/or an Internet Protocol ("IP") network such as the Internet, an intranet, or an extranet. Note that any devices described herein may communicate via one or more such communication networks.

The delamination sensing and locating platform 150 may store information into and/or retrieve information from various data sources, such as the computer data store 110 and/or user platforms 170. The various data sources may be locally stored or reside remote from the delamination sensing and locating platform 150. Although a single delamination sensing and locating platform 150 is shown in FIG. 1, any number of such devices may be included. Moreover, various devices described herein might be combined according to embodiments of the present invention. For example, in some embodiments, the delamination sensing and locating platform 150 and one or more data sources 110 might comprise a single apparatus. The delamination sensing and locating platform 150 functions may be performed by a constellation of networked apparatuses, in a distributed processing or cloud-based architecture.

A user may access the system 100 via one of the user platforms 170 (e.g., a Personal Computer ("PC"), tablet, or smartphone) to view information about and/or manage delamination information in accordance with any of the embodiments described herein. In some cases, an interactive graphical display interface may let an operator define and/or adjust certain parameters and/or provide or receive automatically generated recommendations or results from the delamination sensing and locating platform 150.

According to some embodiments, a signal processing unit 160 in the delamination sensing and locating platform 150 may receive and process data from sensors. The signal processing unit 160 and/or a threshold exceedance detector 162 may look for certain characteristics in the sensor data. Moreover, a delamination location estimation unit 164 might predict where a delamination event may have occurred (e.g., at a particular location in a structure of the physical system 120) and a delamination alert output 166 may transmit a delamination assessment and/or prediction as appropriate.

Figure 2:
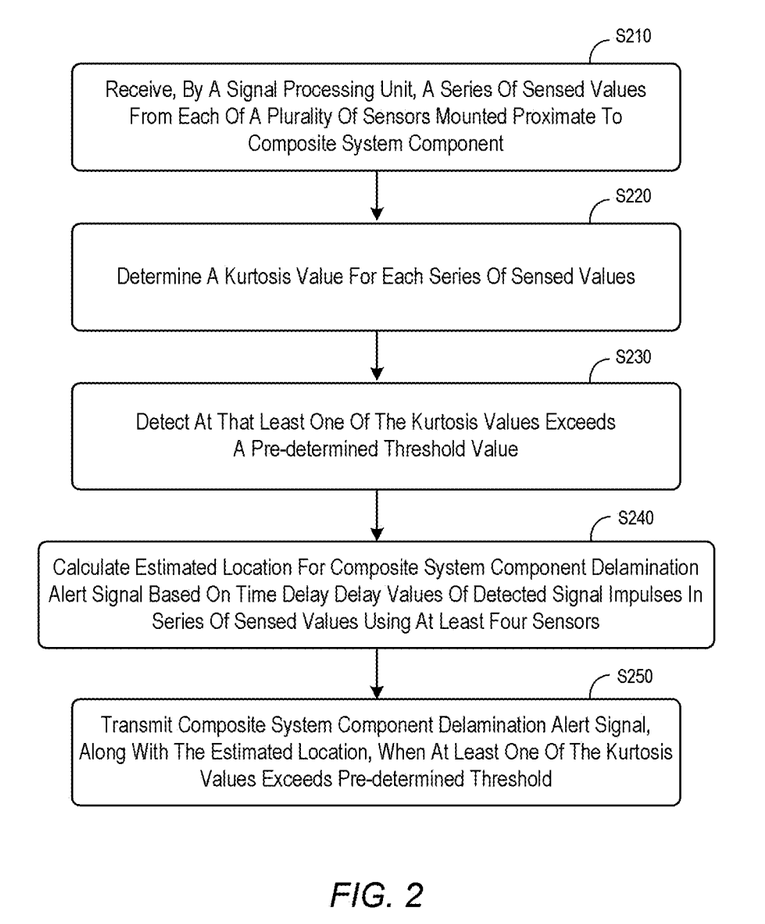
FIG. 2 is a delamination assessment and/or prediction method according to some embodiments.

For example, FIG. 2 illustrates a method that might be performed by some or all of the elements of the system 100 described with respect to FIG. 1. The flow charts described herein do not imply a fixed order to the steps, and embodiments of the present invention may be practiced in any order that is practicable. Note that any of the methods described herein may be performed by hardware, software, or any combination of these approaches. For example, a computer-readable storage medium may store thereon instructions that when executed by a machine result in performance according to any of the embodiments described herein.

At 5210, a signal process unit may receive a series of sensed values from each of a plurality of sensors mounted proximate to a composite system component (e.g., an aircraft body part). According to some embodiments, at least one of the sensors may be placed on or impregnated within the composite system component. One or more of the sensors might comprise, for example, an acoustic sensor, a seismic sensor, an accelerometer transducer sensor, and/or a multi-point transducer. At 5220, the signal processing unit may determine a kurtosis value for each series of sensed values.

At 5230, a threshold exceedance detector may detect if at least one of the kurtosis values exceeds a pre-determined threshold value. At 5240, a delamination location estimation unit may calculate an estimated location of a composite system component delamination alert signal based on calculated time difference delay values of detected signal impulses in the series of sensed values using at least four of the plurality of sensors. The estimated location might be, for example, calculated based at least in part on geometric dilution of precision techniques.

At 5250, a delamination alert output may transmit a composite system component delamination alert signal, along with the estimation location, when at least one of the kurtosis values exceeds the pre-determined threshold. The composite system component delamination alert signal might be, for example, responsive to at least one of a shock signal signature (e.g., in the series of sensed values from at least one of the sensors), a jerk signal signature, a crackling signal signature, a cracking signal signature, and/or a relatively low speed, blunt impact to the composite system component.

Figure 3:
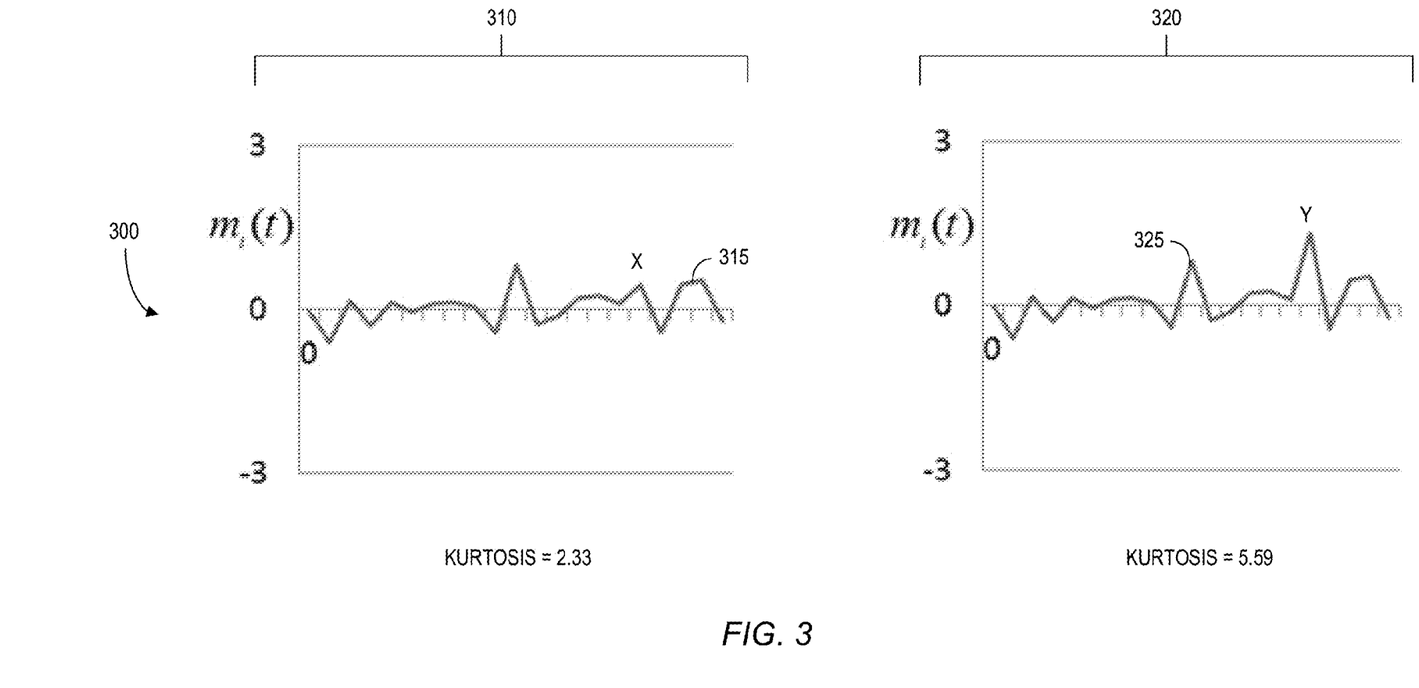
FIG. 3 illustrates multi-point transducer outputs in accordance with some embodiments.

FIG. 3 illustrates multi-point transducer outputs 300 in accordance with some embodiments.

To realize a simulated model, such as a "digital twin," of a complex structure such as an aircraft, it may be necessary to model the states of all of the structure's parts. One problem with such modeling may be associated with an estimation of the health of a composite volume comprising a laminate because as the composite volume is a single body and can suffer internal delamination damage that is externally invisible. One significant issue when attempting to automatically and accurately detect such damage is the choice of an appropriate sensor that may be integrated into the structure in order to assess its health.

Composites, which play a key role in much of modern commercial aviation, have laminates that may suffer delamination under low speed blunt impacts due to poor through-thickness strength. This can provide a challenge in accurately assessing a part's physical condition and estimated RUL. There are a number of techniques by which a large volume of composite may be inspected. These techniques, however, require significant time, cost, and planned downtime. It may be advantageous to instead limit inspections to relatively small volumes (and only after an indication that non-externally visible delamination potentially exists). One such indication might occur when a composite surface has suffered a blunt impact, such as a low speed collision with ground service equipment such as a baggage vehicle fuel delivery truck.

Because the exact characteristics of random noise present in a structure is likely to be unknown, some embodiments described herein may be associated with a statistic that is sensitive to sharp, impulse-like signature characteristics of cracking or crackling that may be indicative of delamination within a composite material (but yet remain robustly insensitive to many other structural noises). To detect such a signature, signal processing using higher central moments may be of value. For example, the kurtosis of a series of values is the ratio of the fourth cumulant to the square of the variance (and, when the kurtosis is defined in this manner, it will clearly always be a non-negative value).

The sensitivity and suitability of the kurtosis for the purposes of embodiments described herein is illustrated in FIG. 3 where a series of twenty-one individual transducer output values $m_i(t)$ are provided 300. Note that two graphs 310, 320 each include identical $m_i(t)$ values with a single exception: the signal 315 in the left graph 310 has a value "0.45." (represented with an X in FIG. 3) while that individual value has been replaced with "1.3" in the signal 325 in the right graph 320 (represented with a Y in FIG. 3). The kurtosis for the sequence of the twenty-one values in the left graph 310 is "2.33" and the kurtosis for the sequence of the twenty-one values in right second graph 320 is "5.59." Using signal detection techniques that are well known in the art, a threshold may be set such that the probability that the kurtosis of a sequence of values will exceed that threshold, under some relatively mild conditions concerning the nature of the process producing the sequence of values, is high only if there are one or more impulse-like values in that particular sequence of values.

Figure 4:
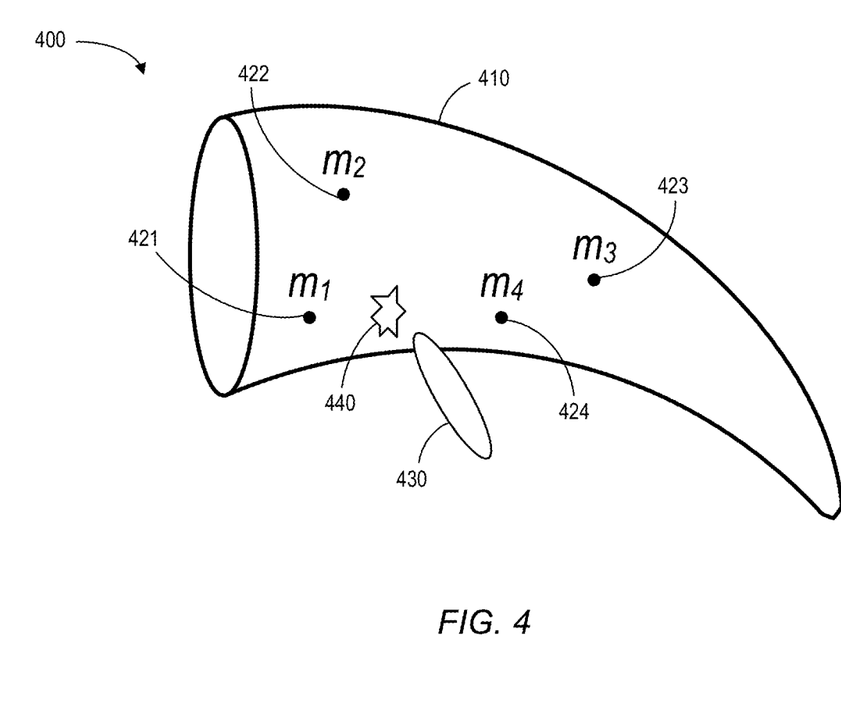
FIG. 4 is an example of a portion of a delamination assessment and/or prediction system according to some embodiments.
Figure 5:
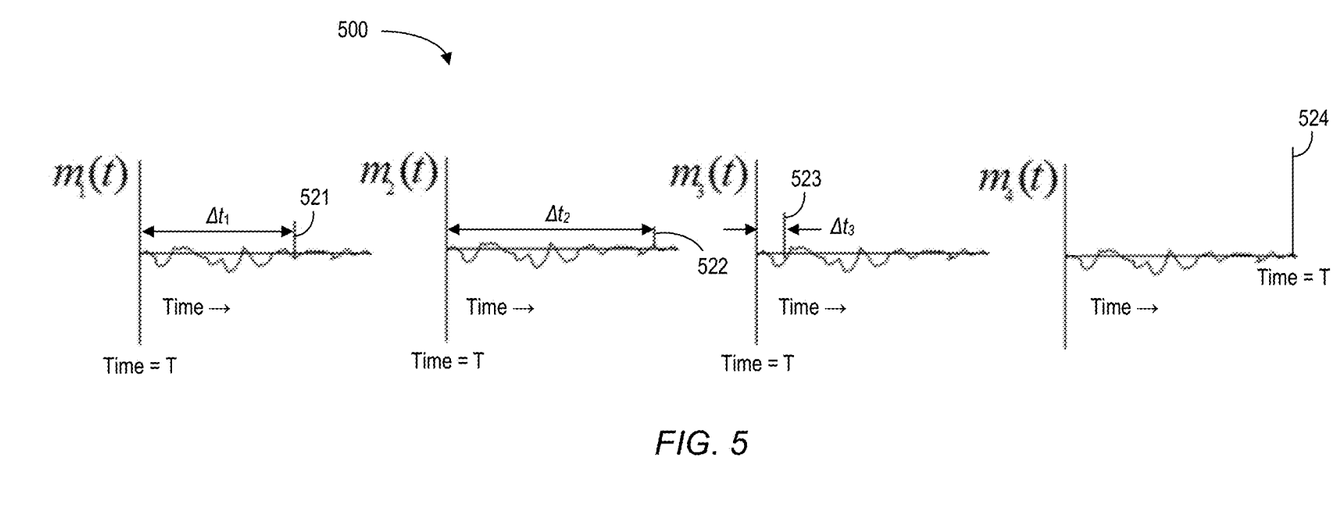
FIG. 5 illustrates typical time outputs from transducers in accordance with some embodiments.

A portion of a delamination assessment and/or prediction system 400 is illustrated in FIG. 4. In particular, a composite system component 410 contains a laminate. Placed on or impregnated within the composite system component 410 is a set of transducers $m_1$, $m_2$, $m_3$, $m_4$ (elements 421, 422, 423, 424 respectively). These transducers 421, 422, 423, 424 may be connected to the Internet of Things (or "IoT," not shown in FIG. 4) by a connection means (also not shown in FIG. 4). FIG. 5 displays typical time outputs 500 of the transducers 421, 422, 423, 424, including an output indicative, by a spike 521, 522, 523, 524, of a transduced impulse.

According to some embodiments, the outputs of the transducers 500 may be monitored and signal processing may be performed on those monitored outputs to detect the presence of impulse spikes 521, 522, 523, 524 signifying the likelihood of a delamination 440 caused by blunt impact with an object 430. The signal processing may be done at a computational facility remote from the composite system component 410 or a local computation facility.

On detection of a kurtosis threshold exceedance, the outputs of 421, 422, 423, 424 are further processed to determine the relative times that the transducers reported the impulse value that caused the kurtosis threshold to be exceeded. These times delay values ($\Delta t_1$, $\Delta t_2$, $\Delta t_3$, $\Delta t_4$ in FIG. 5) may be used to estimate the location of the potential delamination 440 within the composite system component 410. This estimation may be done by techniques well known in the art and placement of the transducers 421, 422, 423, 424 on or within the composite system component 410 may be guided by Geometric Dilution of Precision ("GDOP") techniques for mitigating location errors.

Thus, according to some embodiments a possible delamination event may be detected based on one or more kurtosis exceedances. Moreover, the location of the delamination event may be determined using Time Difference Of Arrival ("TDOA") techniques. In particular, if an event happens (resulting in an impulse or short-duration signal detected by a sensor) it may be assumed to propagate through the medium (e.g., the composite structure) in all directions at substantially the same speed. It may then be detected by the nearest receiver, which may be a sensor or acoustic transducer. Note that transducers in a composite structure may constantly produce digitized samples of their inputs. As a result, the impulse may become digitized and reside within at least one of the samples produced by each of the sensors. Because the sensors may be at different distances from the delamination event, it may be assumed that the nearest sensor will produce the biggest sampled value when detecting the impulse (because increased propagation will diminish the value of the disturbance). Further note that each sensor may continuously form the kurtosis of its most recent N samples. If the impulse is sufficiently large and short in duration, then at least the nearest sensor may report a kurtosis exceedance. When the first sensor (assumedly the sensor nearest to the potential delamination) reports a kurtosis exceedance, all of the other sensors may be examined and the times between the first sensor's exceedance and the times that the impulse shows up at the other sensors (even if those other sensors did not detect a kurtosis exceedance) will form a plurality of time differences. To estimate the three-dimensional location of the potential delamination event, the system may utilize three sensors beyond the first one that triggered the time delay measurements (e.g., utilizing a total of at least four sensors). In the example 500 of FIG. 5, four sensors produce four series of sampled values, $m_1(t)$, $m_2(t)$, $m_3(t)$, $m_4(t)$. Sensor four first reports a kurtosis exceedance caused by an impulse 524. In this processing example, the impulse 524 is referenced as the N-th sample of sensor 4 which occurred at time=T. The system then looks for where the impulse shows up at the other sensors and measures the time, with respect to T, that the impulse shows at the other sensors. In other words, the impulse shows up at the other sensors after time=T and the delay between time=T and the i-th sensor observing the impulse is $\Delta t_i$. For the example illustrated in FIG. 5, the impulse next shows up at sensor 3 as indicated by 523, next at sensor 1, as indicated by 521, and finally at sensor 2 as indicated by 522. The time delays $\Delta t_1$, $\Delta t_2$, $\Delta t_3$ are thus calculated from the times the impulse shows up in sensors 1, 2, and 3 with respect to time=T which is the time that the impulse was first detected by sensor 4.

Figure 6:
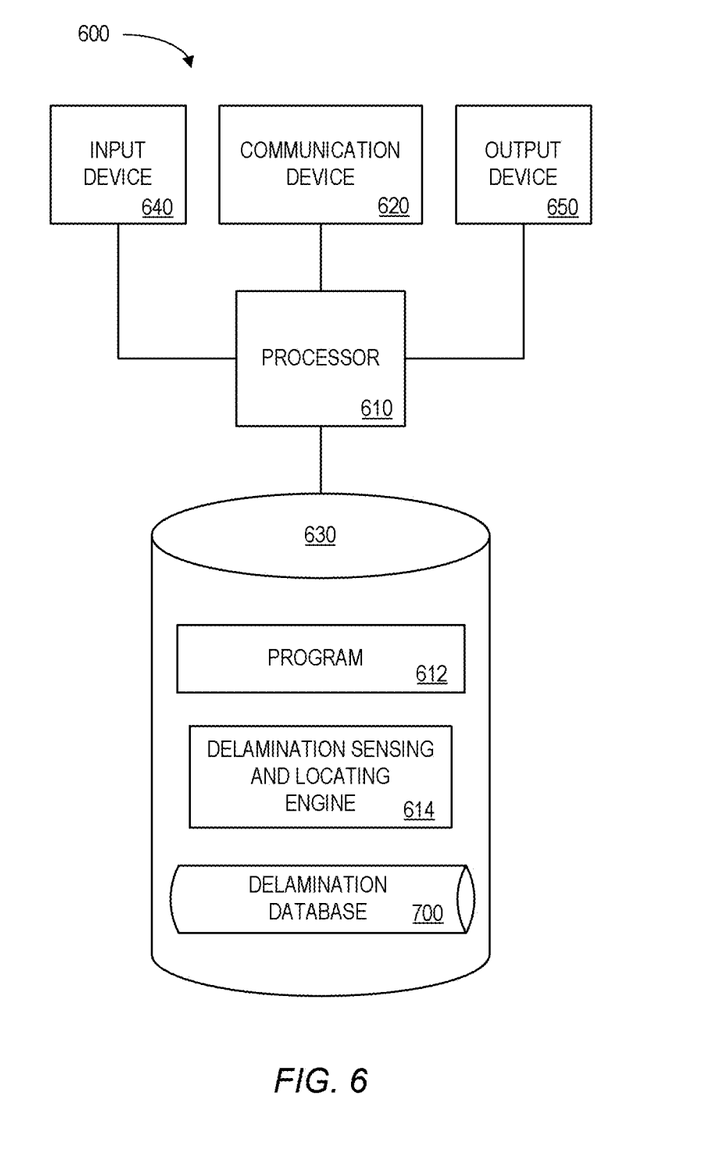
FIG. 6 is a block diagram of a delamination assessment and/or prediction platform according to some embodiments of the present invention.

The embodiments described herein may be implemented using any number of different hardware configurations. For example, FIG. 6 is a block diagram of a delamination sensing and locating platform 600 that may be, for example, associated with the system 100 of FIG. 1. The delamination sensing and locating platform 600 comprises a processor 610, such as one or more commercially available Central Processing Units ("CPUs") in the form of one-chip microprocessors, coupled to a communication device 620 configured to communicate via a communication network (not shown in FIG. 6). The communication device 620 may be used to communicate, for example, with one or more remote sensors, user platforms, digital twins, computations associates, etc. The delamination sensing and locating platform 600 further includes an input device 640 (e.g., a computer mouse and/or keyboard to input adaptive and/or predictive modeling information) and/an output device 650 (e.g., a computer monitor to render a display, provide alerts, transmit recommendations, and/or create reports). According to some embodiments, a mobile device, monitoring physical system, and/or PC may be used to exchange information with the delamination sensing and locating platform 600.

The processor 610 also communicates with a storage device 630. The storage device 630 may comprise any appropriate information storage device, including combinations of magnetic storage devices (e.g., a hard disk drive), optical storage devices, mobile telephones, and/or semiconductor memory devices. The storage device 630 stores a program 612 and/or a delamination sensing and locating engine 614 for controlling the processor 610. The processor 610 performs instructions of the programs 612, 614, and thereby operates in accordance with any of the embodiments described herein. For example, the processor 610 may receive, from each of a plurality of sensors mounted proximate to a composite system component, a series of sensed values. The processor 610 may then determine a kurtosis value for each series of sensed values and detect if at least one of the kurtosis values exceeds a pre-determined threshold value. The processor 610 may also calculate an estimated location of a composite system component delamination alert signal based on calculated relative time delay values of detected signal impulses in the series of sensed values using at least four of the plurality of sensors. The processor 610 may then transmit a composite system component delamination alert signal, along with the estimated location, when at least one of the kurtosis values exceeds the pre-determined threshold.

The programs 612, 614 may be stored in a compressed, uncompiled and/or encrypted format. The programs 612, 614 may furthermore include other program elements, such as an operating system, clipboard application, a database management system, and/or device drivers used by the processor 610 to interface with peripheral devices.

As used herein, information may be "received" by or "transmitted" to, for example: (i) the delamination sensing and locating platform 600 from another device; or (ii) a software application or module within the delamination sensing and locating platform 600 from another software application, module, or any other source.

In some embodiments (such as the one shown in FIG. 6), the storage device 630 further stores a delamination database 700. An example of a database that may be used in connection with the delamination sensing and locating platform 600 will now be described in detail with respect to FIG. 7. Note that the database described herein is only one example, and additional and/or different information may be stored therein. Moreover, various databases might be split or combined in accordance with any of the embodiments described herein.

Figure 7:
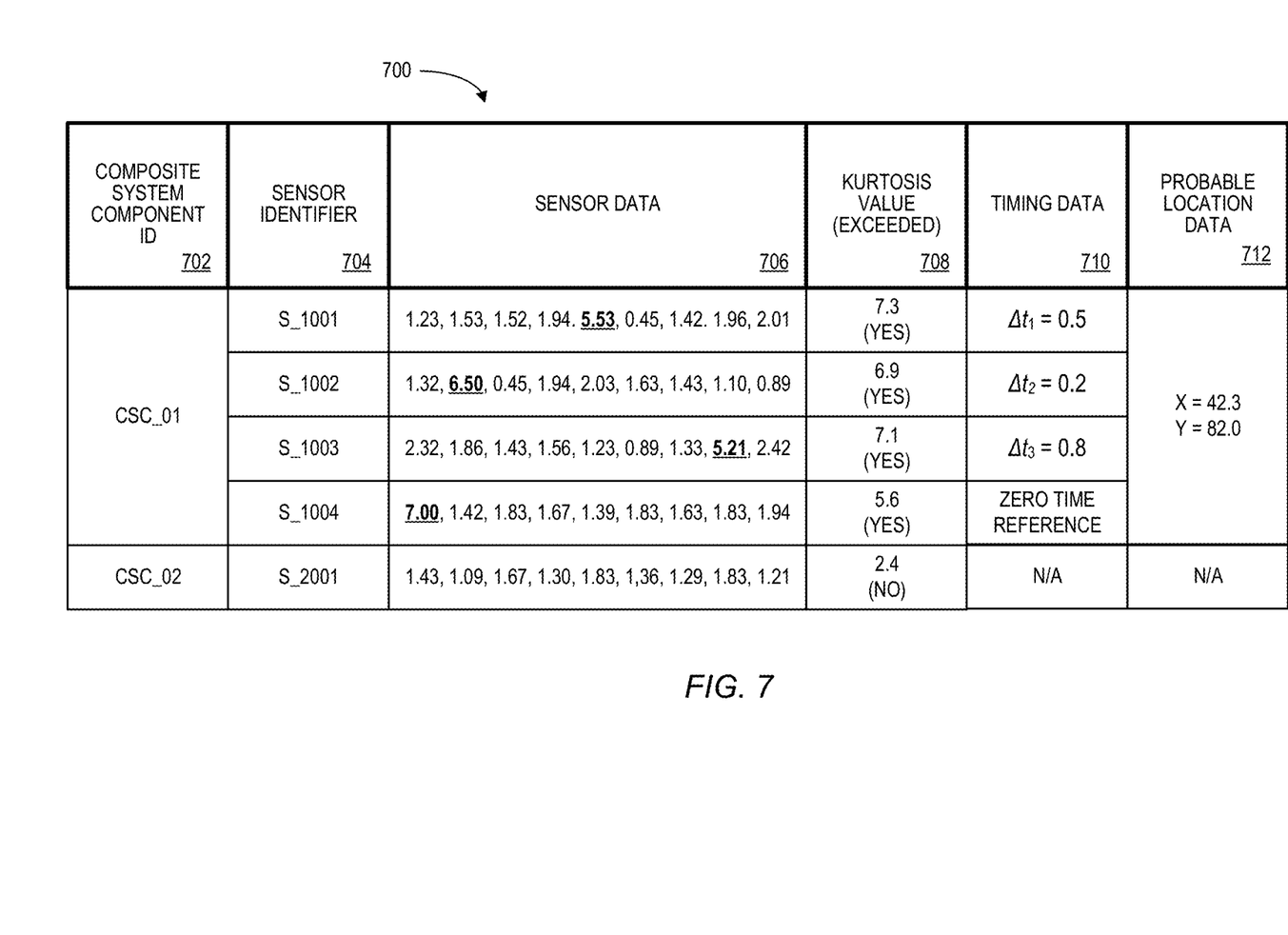
FIG. 7 is a tabular portion of a delamination database according to some embodiments.

Referring to FIG. 7, a table is shown that represents the delamination database 700 that may be stored at the delamination sensing and locating platform 600 according to some embodiments. The table may include, for example, entries identifying sensor measurement associated with a physical system. The table may also define fields 702, 704, 706, 708, 710, 712 for each of the entries. The fields 702, 704, 706, 708, 710, 712 may, according to some embodiments, specify: a composite system component identifier 702, a sensor identifier 704, sensor data 706, a kurtosis value 708, timing data 710, and probable location data 712. The delamination database 700 may be created and updated, for example, when a new physical system is monitored, sensors report values, operating conditions change, etc.

The composite system component identifier 702 may be, for example, a unique alphanumeric code identifying a laminate component in a physical system (e.g., associated with the surface of an aircraft tail section). The sensor identifier 704 indicates a set of sensors that are mounted proximate to that laminate component (e.g., sensors "S_1001," "S_1002," "S_1003," and "S_1004" are mounted proximate to "CSC_01"). The sensor data 706 comprises a series of values reported from each sensor. For example, sensor "S_1002" (as illustrated by the second entry in the table 700) has reported values: 1.32, 6.50, 0.45, 1.94, etc. In the illustration of FIG. 7, sensor values associated with an impulse (e.g., as a result of delamination) are represented with bold and underlined text. The kurtosis value 708 is calculated by signal processing unit based on the sensor data 706, and may include an indication of whether or not a threshold value has been exceeded. Note that the data values illustrated in FIG. 7 are only provided to clarify understanding of the present invention (and, for example, the kurtosis values 708 do not reflect actual calculations based on the illustrated series of sensor data values 706). The timing data 710 may be associated with timing values of impulses within the sensor data 706 (which may, in turn correlate with distances to a delamination location). For example, sensor identifier 704 "S_1004" may have been the first to detect the potential delamination event (e.g., reflected by the "7.00" value in the sensor data 706) and, as a result, may be established as the "Zero Time Reference" from which other timing data 710 delays may be measured. The timing data 710 can then be used to generate probable location data 712 associated with a delamination alert signal (e.g., a part number, an X, Y coordinate location, etc.).

Figure 8:
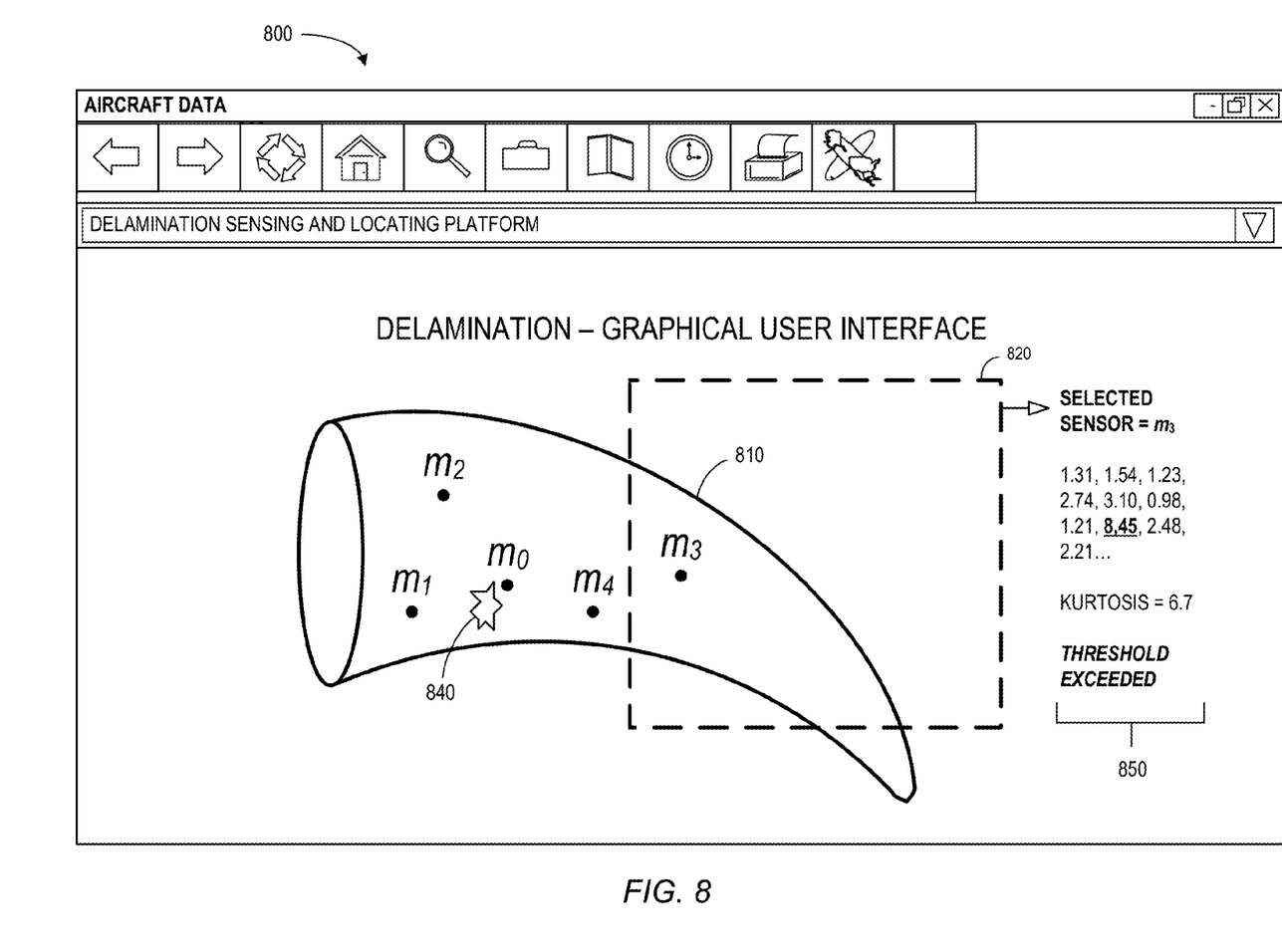
FIG. 8 illustrates an interactive delamination graphical user interface display according to some embodiments.

FIG. 8 illustrates an interactive graphical user interface display 800 according to some embodiments. The display 800 may include a graphical rendering 810 of a physical object 810 and a user selectable area 820 that may be used to identify portions of the physical object, sensors $m_0$, $m_1$, $m_2$, $m_3$, $m_4$ mounted on or within the physical object 810, and/or a delamination location 840. A data readout area 830 might provide further details about the selections (e.g., regarding sensors within the identified portion, sensed data values, impulses, kurtosis, exceedance information, etc.).

Figure 9:
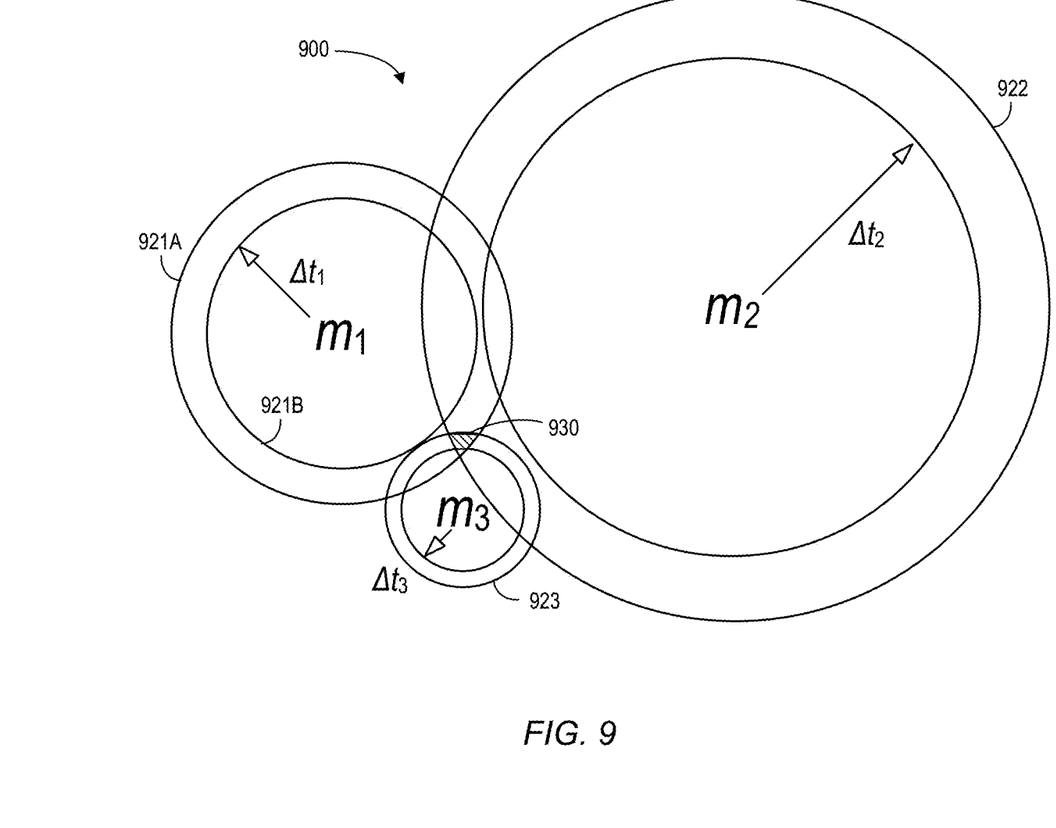
FIG. 9 illustrates a delamination location technique in accordance with some embodiments.

FIG. 9 illustrates a delamination location technique 900 in accordance with some embodiments. In this example, four sensors $m_0$, $m_1$, $m_2$, $m_3$ have each recognized an impulse possibly associated with delamination detection. Sensor $m_0$ is the first sensor to recognize the event, and the impulse from each of the other three sensors is associated with a time difference delay value of $\Delta t_1$, $\Delta t_2$, $\Delta t_3$, respectively, as measured from a "zero time reference" representing the time the impulse first appeared at sensor $m_0$. Assuming that acoustic, vibrational, etc. values sensed by a sensor travel through the physical object at a relatively constant rate, these time difference delay values $\Delta t_1$, $\Delta t_2$, $\Delta t_3$ may be used to approximate physical distances between the locations of the sensors $m_0$, $m_1$, $m_2$, $m_3$ and the location of the delamination that caused the impulse signals. For example, the first sensor $m_1$ might be predicted to be between a maximum distance 921A and a minimum distance 921B from where delamination occurred. Likewise, the second sensor $m_2$ and the third sensor $m_3$ might be associated with different predicted distance ranges 922, 923. An intersection of these three rings of predicted ranges 921, 922, 923 may then be determined to be the likely location of delamination (represented by shaded area 930 in FIG. 9) that can be reported along with a delamination alert signal.

With the advancement of sensors, communications, and computational modeling, it may be possible to consider multiple components of a system, each having its own micro-characteristics and not just average measures of a plurality of components associated with a production run or lot. Moreover, it may be possible to very accurately monitor and continually assess the health of individual components, predict their remaining lives, and consequently estimate the health and RUL of systems that employ them. This would be a significant advance for applied prognostics, and discovering a system and methodology to do so in an accurate and efficient manner will help reduce unplanned down time for complex systems (resulting in cost savings and increased operational efficiency). It may also be possible to achieve a more nearly optimal control of an asset if the life of the parts can be accurately determined as well as any degradation of the key components. According to some embodiments described herein, this type of information, including delamination alerts and location data, may be provided by a "digital twin" of a twinned physical system.

A digital twin may estimate a remaining useful life of a twinned physical system using sensors, communications, modeling, history, and/or computation. It may provide an answer in a time frame that is useful (that is, meaningfully prior to a projected occurrence of a failure event or suboptimal operation). It might comprise a code object with parameters and dimensions of its physical twin's parameters and dimensions that provide measured values, and keeps the values of those parameters and dimensions current by receiving and updating values via outputs from sensors embedded in the physical twin. The digital twin may be, according to some embodiments, upgraded upon occurrence of unpredicted events and other data, such as the discovery and identification of exogenous variables, which may enhance accuracy. The digital twin may also be used to prequalify a twinned physical system's reliability for a planned mission. The digital twin may comprise a real time efficiency and life consumption state estimation device. It may comprise a specific, or "per asset," portfolio of system models and asset specific sensors. It may receive inspection and/or operational data and track a single specific asset over its lifetime with observed data and calculated state changes. Some digital twin models may include a functional or mathematical form that is the same for like asset systems, but will have tracked parameters and state variables that are specific to each individual asset system.

A twinned physical system may be either operating or non-operating. When non-operating, the digital twin may remain operational and its sensors may keep measuring their assigned parameters (including, for example, parameters associated with delamination sensing). In this way, a digital twin may still make accurate assessments and predictions even when the twinned physical system is altered or damaged in a non-operational state. Note that if the digital twin and its sensors were also non-operational, the digital twin might be unaware of significant events of interest.

A digital twin may be placed on a twinned physical system and run autonomously or globally with a connection to external resources using the IoT or other data services. Note that an instantiation of the digital twin's software could take place at multiple locations. A digital twin's software could reside near the asset and used to help control the operation of the asset. Another location might be at a plant or farm level, where system level digital twin models may be used to help determine optimal operating conditions for a desired outcome, such as minimum fuel usage to achieve a desired power output of a power plant. In addition, a digital twin's software could reside in the cloud, implemented on a server remote from the asset. The advantages of such a location might include scalable computing resources to solve computationally intensive calculations required to converge a digital twin model producing an output vector $\bar{y}$.

It should be noted that multiple but different digital twin models for a specific asset, such as an aircraft, could reside at all three of these types of locations. Each location might, for example, be able to gather different data, which may allow for better observation of the asset states and hence determination of the tuning parameters, $\bar{a}$, especially when the different digital twin models exchange information.

A "Per Asset" digital twin may be associated with a software model for a particular twinned physical asset. The mathematical form of the model underlying similar assets may, according to some embodiments, be altered from like asset system to like asset system to match the particular configuration or mode of incorporation of each asset system. A Per Asset digital twin may comprise a model of the structural components, their physical functions, and/or their interactions. A Per Asset digital twin might receive sensor data from sensors that report on the health and stability of a system, environmental conditions, and/or the system's response and state in response to commands issued to the system. A Per Asset digital twin may also track and perform calculations associated with estimating a system's remaining useful life.

A Per Asset digital twin may comprise a mathematical representation or model along with a set of tuned parameters that describe the current state of the asset. This is often done with a kernel-model framework, where a kernel represents the baseline physics of operation or phenomenon of interest pertaining to the asset. The kernel has a general form of:

$$\bar{y}=f(\bar{a},\bar{x})$$

where $\bar{a}$ is a vector containing a set of tuning parameters that are specific to the asset and its current state. Examples may include component efficiencies in different sections of an aircraft body part or gas turbine. The vector x contains the kernel inputs, such as operating conditions (fuel flow, altitude, ambient temperature, pressure, etc.). Finally, the vector $\bar{y}$ is the kernel outputs which could include sensor measurement estimates or asset states (part life damage states, etc.).

When a kernel is tuned to a specific asset, the vector $\bar{a}$ is determined, and the result is called the Per Asset digital twin model. The vector $\bar{a}$ will be different for each asset and will change over its operational life. The Component Dimensional Value table ("CDV") may record the vector $\bar{a}$. It may be advantageous to keep all computed vector $\bar{a}$'s versus time to then perform trending analyses or anomaly detection.

A Per Asset digital twin may be configured to function as a continually tuned digital twin, a digital twin that is continually updated as its twinned physical system is on-operation, an economic operations digital twin used to create demonstrable business value, an adaptable digital twin that is designed to adapt to new scenarios and new system configurations and may be transferred to another system or class of systems, and/or one of a plurality of interacting digital twins that are scalable over an asset class and may be broadened to not only model a twinned physical asset but also provide control over the asset.

Figure 10:
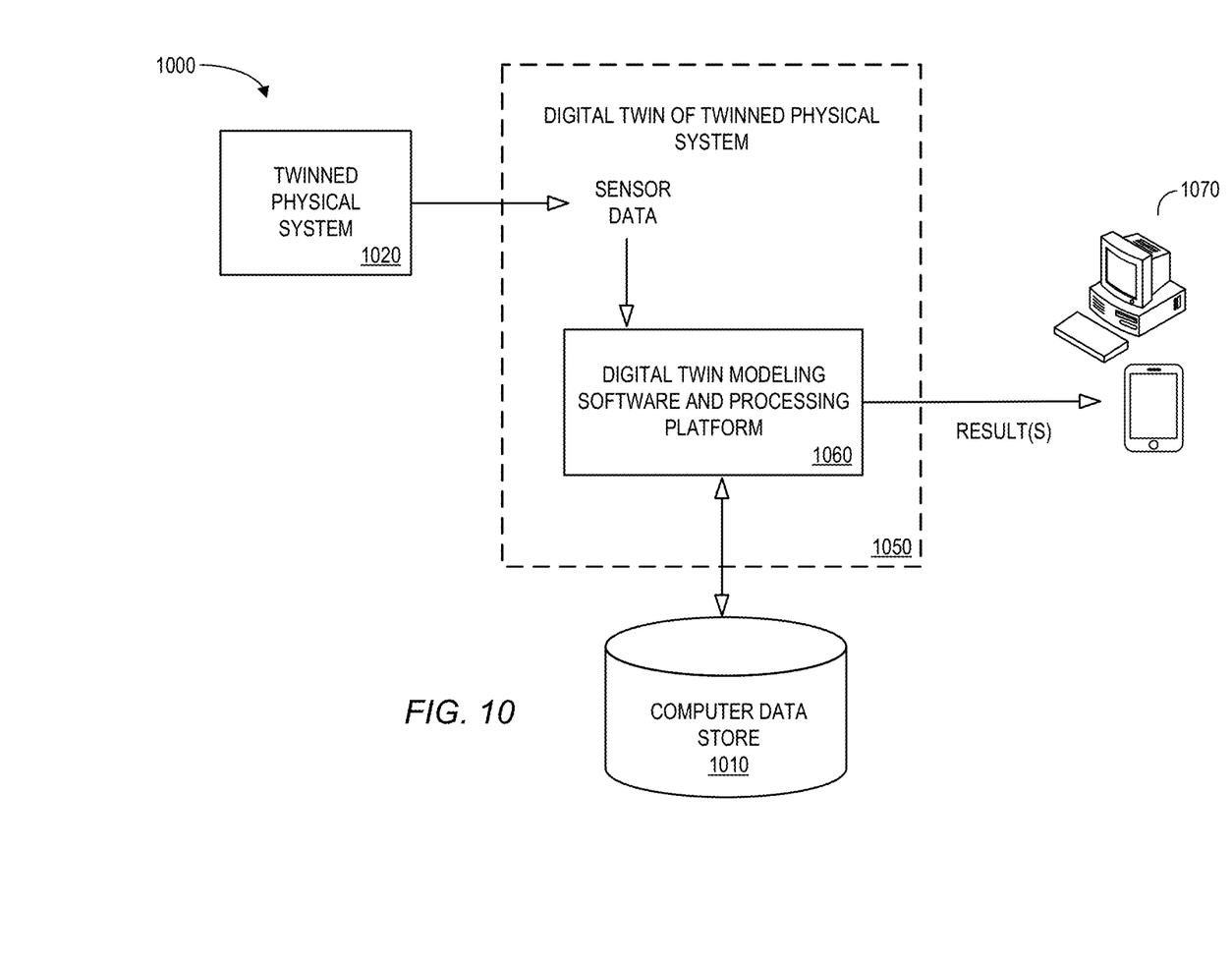
FIG. 10 is a high-level block diagram of a digital twin system that may be provided in accordance with some embodiments.

FIG. 10 is a high-level architecture of a system 1000 in accordance with some embodiments. The system 1000 includes a computer data store 1010 that provides information to a digital twin of a twinned physical system 1050. Data in the data store 1010 might include, for example, information about a twinned physical system 1020, such as historic body part sensor information about a number of different aircraft body parts and prior aircraft flights (e.g., external temperatures, exhaust gas temperatures, body part model numbers, takeoff and landing airports, etc.).

The digital twin of a twinned physical system 1050 may, according to some embodiments, access the data store 1010, and utilize a probabilistic model creation unit to automatically create a predictive model that may be used by a digital twin modeling software and processing platform to create an alert, prediction, and/or result that may be transmitted to various user platforms 1070 as appropriate (e.g., for display to a user). As used herein, the term "automatically" may refer to, for example, actions that can be performed with little or no human intervention.

As used herein, devices, including those associated with the system 1000 and any other device described herein, may exchange information via any communication network which may be one or more of a LAN, a MAN, a WAN, a proprietary network, a PSTN, a WAP network, a Bluetooth network, a wireless LAN network, and/or an IP network such as the Internet, an intranet, or an extranet. Note that any devices described herein may communicate via one or more such communication networks.

The digital twin of a twinned physical system 1050 may store information into and/or retrieve information from various data sources, such as the computer data store 1010 and/or user platforms 1070. The various data sources may be locally stored or reside remote from the digital twin of a twinned physical system 1050. Although a single digital twin of a twinned physical system 1050 is shown in FIG. 10, any number of such devices may be included. Moreover, various devices described herein might be combined according to embodiments of the present invention. For example, in some embodiments, the digital twin of a twinned physical system 1050 and one or more data sources might comprise a single apparatus. The digital twin software of twinned physical system 1050 function (including delamination sensing and locating) may be performed by a constellation of networked apparatuses, in a distributed processing or cloud-based architecture.

Thus, some embodiments may provide systems and methods to facilitate delamination assessments and/or predictions for a physical system in an automatic and accurate manner.

The following illustrates various additional embodiments of the invention. These do not constitute a definition of all possible embodiments, and those skilled in the art will understand that the present invention is applicable to many other embodiments. Further, although the following embodiments are briefly described for clarity, those skilled in the art will understand how to make any changes, if necessary, to the above-described apparatus and methods to accommodate these and other embodiments and applications.

Although specific hardware and data configurations have been described herein, note that any number of other configurations may be provided in accordance with embodiments of the present invention (e.g., some of the information associated with the databases described herein may be combined or stored in external systems). For example, although some embodiments are focused on aircraft parts, any of the embodiments described herein could be applied to other types of assets, such as wind, gas, or water turbines, support structures, etc.

Some embodiments described herein have used time delay values to approximate a distance between a sensor and a delamination event. According to other embodiments, a decrease in a magnitude of a detected impulse signal might likewise be used to approximate such a distance.

Moreover, some embodiments have been described as using information from at least four sensors (with one sensor providing the first detection of a delamination event and the other three sensors providing time delay values to locate an area where the event occurred). Other embodiments, however, might use information from three sensors. In this case, one sensor could still provide the first detection of the event while the other two sensors define two potential areas where the event might have occurred. For example, in FIG. 9 of the present application the rings associated with $m_1$ and $m_2$ might intersect at two different locations (one of which might be the location of the delamination event). Further, based on the geometry of an actual component being monitored, one of those two potential locations might be physically impossible (e.g., one location might not even be on the aircraft wing). As still another example, some embodiments may use only two sensors. In this case, one sensor may provide the first detection of the event while the other sensor provides information that could be used to define a curved band (or two curved bands) of potential areas where the delamination event might have occurred. As another approach, one or more sensors might provide directional information about an impulse in addition to the pulse's magnitude (and a likely location might be based at least in part on this directional information). In addition, although some embodiments have been described with respect to estimating a 2-D location, any of the embodiments described herein might be associated with a 3-D location of a potential delamination event (e.g., and might include a depth of a potential delamination event from the surface of a component being monitored).

In yet another embodiment, the plurality of sensors may exceed four. In that case, the location of the possible location of the delamination event, e.g., the region 930 in FIG. 9, may be narrowed in volume by using methods well known in the art such as least means squares sensor fusion techniques and Geometric Dilution Of Precision ("GDOP") calculations.

The present invention has been described in terms of several embodiments solely for the purpose of illustration. Persons skilled in the art will recognize from this description that the invention is not limited to the embodiments described, but may be practiced with modifications and alterations limited only by the spirit and scope of the appended claims.

The invention claimed is:

1. A system to monitor a composite system component, comprising:
   a plurality of sensors mounted proximate to the composite system component;
   a signal processing unit to receive, from each sensor, a series of sensed values associated with the composite system component and to determine a kurtosis value for each series of sensed values;
   a threshold exceedance detector to detect if at least one of the kurtosis values exceeds a threshold value;
   a delamination location estimation unit to calculate an estimated location of a composite system component associated with a delamination alert signal based on calculated time difference delay values of detected signal impulses in the series of sensed values using at least four of the plurality of sensors;
   a delamination alert output to transmit a composite system component delamination alert signal, along with the estimation location, when at least one of the kurtosis values exceeds the threshold;
   wherein the signal processing unit is associated with a digital twin of a twinned physical system, the twinned physical system including the composite system component;
   wherein the digital twin comprises:
   one or more digital twin sensors to sense values of one or more designated parameters of the twinned physical system;
   a computer processor to receive data associated with the one or more digital twin sensors and programmed to:
      for at least a selected portion of the twinned physical system, execute at least one of: (i) a monitoring process to monitor a condition of the selected portion of the twinned physical system based at least in part on the sensed values of the one or more designated parameters, and (ii) an assessing process to assess a remaining useful life of the selected portion of the twinned physical system based at least in part on the sensed values of the one or more designated parameters and
      a communication port coupled to the computer processor to transmit information associated with a result generated by the computer processor,
   wherein the one or more digital twin sensors are to sense values of the one or more designated parameters, and the computer processor is to execute at least one of the monitoring and assessing processes, when the twinned physical system is not operating.

2. The system of claim 1, wherein the estimated location is calculated based at least in part on time differences of arrival.

3. The system of claim 1, wherein at least one sensor is associated with at least one of: (i) an acoustic sensor, (ii) a seismic sensor, (iii) an accelerometer transducer sensor, and (iv) a multi-point transducer.

4. The system of claim 1, wherein the composite system component delamination alert signal is responsive to at least one of: (i) a shock signal signature, (ii) a jerk signal signature, (iii) a crackling signal signature, (iv) a cracking signal signature, and (v) a relatively low speed, blunt impact to the composite system component.

5. The system of claim 1, wherein at least one of the sensors is placed on or impregnated within the composite system component.

6. A computerized method to monitor a composite system component, comprising:
   receiving by a signal processing unit a series of sensed values, associated with the composite system component, from each of a plurality of sensors mounted proximate to the composite system component;
   determining by the signal processing unit a kurtosis value for each series of sensed values;
   detecting, by a threshold exceedance detector, if at least one of the kurtosis values exceeds a threshold value;
   calculating, by a delamination location estimation unit, an estimated location of a composite system component associated with a delamination alert signal based on calculated time difference delay values of detected signal impulses in the series of sensed values using at least four of the plurality of sensors;
   transmitting, via a delamination alert output, a composite system component delamination alert signal, along with the estimated location, when the at least one of the kurtosis values exceeds the threshold;
   wherein the signal processing unit is associated with a digital twin of a twinned physical system, the twinned physical system including the composite system component;
   wherein the digital twin comprises:
   one or more digital twin sensors to sense values of one or more designated parameters of the twinned physical system;
   a computer processor to receive data associated with the one or more digital twin sensors and programmed to:
      for at least a selected portion of the twinned physical system, execute at least one of: (i) a monitoring process to monitor a condition of the selected portion of the twinned physical system based at least in part on the sensed values of the one or more designated parameters, and (ii) an assessing process to assess a remaining useful life of the selected portion of the twinned physical system based at least in part on the sensed values of the one or more designated parameters and
      a communication port coupled to the computer processor to transmit information associated with a result generated by the computer processor,
   wherein the one or more digital twin sensors are to sense values of the one or more designated parameters, and the computer processor is to execute at least one of the monitoring and assessing processes, when the twinned physical system is not operating.

7. The method of claim 6, wherein the estimated location is based at least in part on time differences of arrival.

8. The method of claim 7, wherein at least one sensor is associated with at least one of: (i) an acoustic sensor, (ii) a seismic sensor, (iii) an accelerometer transducer sensor, and (iv) a multi-point transducer.

9. The method of claim 7, wherein the composite system component alert signal is responsive to at least one of: (i) a shock signal signature, (ii) a jerk signal signature, (iii) a crackling signal signature, (iv) a cracking signal signature, and (v) a relatively low speed, blunt impact to the composite system component.

10. The method of claim 6, wherein at least one of the sensors is placed on or impregnated within the composite system component.

11. A non-transitory, computer-readable medium storing instructions that, when executed by a computer processor, cause the computer processor to perform a method to monitor a composite system component, the method comprising:
receiving by a signal processing unit a series of sensed values, associated with the composite system component, from each of a plurality of sensors mounted proximate to the composite system component;
determining by the signal processing unit a kurtosis value for each series of sensed values;
detecting, by a threshold exceedance detector, if at least one of the kurtosis values exceeds a threshold value;
calculating, by a delamination location estimation unit, an estimated location of a composite system component associated with a delamination alert signal based on calculated time difference delay values of detected signal impulses in the series of sensed values using at least four of the plurality of sensors;
transmitting, via a delamination alert output, a composite system component delamination alert signal, along with the estimated location, when the at least one of the kurtosis values exceeds the threshold;
wherein the signal processing unit is associated with a digital twin of a twinned physical system, the twinned physical system including the composite system component;
wherein the digital twin comprises:
one or more digital twin sensors to sense values of one or more designated parameters of the twinned physical system;
a computer processor to receive data associated with the one or more digital twin sensors and programmed to:
for at least a selected portion of the twinned physical system, execute at least one of: (i) a monitoring process to monitor a condition of the selected portion of the twinned physical system based at least in part on the sensed values of the one or more designated parameters, and (ii) an assessing process to assess a remaining useful life of the selected portion of the twinned physical system based at least in part on the sensed values of the one or more designated parameters and
a communication port coupled to the computer processor to transmit information associated with a result generated by the computer processor,
wherein the one or more digital twin sensors are to sense values of the one or more designated parameters, and the computer processor is to execute at least one of the monitoring and assessing processes, when the twinned physical system is not operating.

12. The medium of claim 11, wherein the estimated location is based at least in part on time differences of arrival.

13. The medium of claim 11, wherein at least one sensor is associated with at least one of: (i) an acoustic sensor, (ii) a seismic sensor, (iii) an accelerometer transducer sensor, and (iv) a multi-point transducer.

14. The medium of claim 11, wherein the composite system component alert signal is responsive to at least one of: (i) a shock signal signature, (ii) a jerk signal signature, (iii) a crackling signal signature, (iv) a cracking signal signature, and (v) a relatively low speed, blunt impact to the composite system component.

15. The medium of claim 11, wherein at least one of the sensors is placed on or impregnated within the composite system component.

16. The medium of claim 11, wherein said calculating is based on calculated time difference delay values of detected signal impulses in the series of sensed values using at least five of the plurality of sensors and includes at least one of a least means squares sensor fusion technique and a geometric dilution of precision calculation.

* * * * *